United States Patent [19]

Zanetti et al.

[11] Patent Number: 5,159,932
[45] Date of Patent: Nov. 3, 1992

[54] MYOCARDIAL ISCHEMIA DETECTION SYSTEM

[75] Inventors: John M. Zanetti, Long Lake; David M. Salerno, Minneapolis, both of Minn.

[73] Assignee: Seismed Instruments, Inc., Minneapolis, Minn.

[21] Appl. No.: 833,630

[22] Filed: Feb. 7, 1992

Related U.S. Application Data

[63] Continuation of Ser. No. 690,635, Apr. 24, 1991, abandoned, which is a continuation of Ser. No. 495,262, Mar. 16, 1990, abandoned.

[51] Int. Cl.$^5$ ............................................. A61B 5/04
[52] U.S. Cl. ................................... 128/696; 128/701; 128/710
[58] Field of Search ............... 128/696, 701, 702, 706, 128/710, 661.04

[56] References Cited

U.S. PATENT DOCUMENTS

| | | | |
|---|---|---|---|
| 3,695,253 | 10/1972 | Vielhauer | 128/695 |
| 3,802,253 | 4/1974 | Lee | 128/661.04 |
| 3,841,315 | 10/1974 | Kopp | 128/701 |
| 3,908,639 | 9/1975 | McIntyre | 128/672 |
| 4,378,022 | 3/1983 | Suobank et al. | 128/715 |
| 4,784,153 | 11/1988 | Marks | 128/701 |
| 4,803,996 | 2/1989 | Peel et al. | 128/696 |
| 4,905,706 | 3/1990 | Duff et al. | 128/701 |

FOREIGN PATENT DOCUMENTS 0357275  3/1990  European Pat. Off. ............ 128/701

OTHER PUBLICATIONS

Spectral Analysis of Second Heart Sound In Normal Children By Selective Linear Preduction Coding; by W. T. Hartwell 6-2.
A 16-Bit Microcomputer Based Biomedical Signal Processor; by Antal A. Sarkady and Errol E. Wallingford.
Algorithm for Detecting The First And The Second Heart Sounds By Spectral Tracking; by Iwata et al.
A Quantative Description Of The Aortic Ejection Click And First Heart Sound; by Showalter.
Ballistocardiography: Past, Present and Future; by W. J. A. Goedhard.
Transactions Paper on Instrumentation For The Diagnosis Of Coronary-Artery Disease; by D. F. Moyer, G. D. Talbott.
A Computerized System for Monitoring Systolic Time Intervals From Esophageal Accelerograms; by Ralph S. Wiley, Lewis B. Wolfenson, and Lee S. Shepard.
Dorland's Illustrated Medical Dictionary, 26th Edition, 1985, p. 1186.
"Seismocardiography in Assessment of Physical Fitness of Sportsmen".
"Determination of Some Time Intervals of the Cardiac Cycle by the Method of Seismocardiography".
"Classification of Changes in the Electrocardiogram in Muscle Loading in a Healthy Human".
"Pulmonary Blood Flow in Healthy Childred Aged 11-13 from Data of Impedance Zonal Rheoplethysmography".
"Seismocardiograph Investigations in Man and in Some Experimental Animals".
"Phasic Structure of the Cardiac Cycle in an Intrauterine Fetus According to Seismocardiographic Findings".
"Diagnosis of the Tricuspidal Defects by the Registration of Low-Frequency Oscillations in the Pericardial Region".
"Piezoelectric Ceramic Transducer 'Pul's'".
"Esophageal Acceleration and the Cardiovascular System".
"A Computerized System for Monitoring Systolic Time Intervals from Esophageal Accelerograms".
"Oesophageal probe for heart and temperature monitoring during anaesthesia".

*Primary Examiner*—William E. Kamm
*Assistant Examiner*—George Manuel
*Attorney, Agent, or Firm*—Merchant, Gould, Smith, Edell, Welter & Schmidt

[57] ABSTRACT

A method and apparatus for non invasively monitoring the motion of the patient's heart, to detect and display ischemia induced variations in the heart's motion which indicate coronary artery disease.

21 Claims, 8 Drawing Sheets

MYOCARDIAL ISCHEMIA DETECTION SYSTEM

CROSS-REFERENCE TO RELATED APPLICATIONS

The present application is a continuation of U.S patent application Ser. No. 07/690,635 filed Apr. 24, 1991, now abandoned which is a continuation of U.S. patent application Ser. No. 07/495,262 filed Mar. 16, 1990 now abandoned.

BACKGROUND OF THE INVENTION

1. Field of The Invention

The present invention relates to a method and apparatus for detecting myocardial ischemia and more particularly to a system for the non-invasive detection and display of a ventricular wall motion signal for diagnostic purposes.

2. Brief Description of The Prior Art

Coronary artery disease (CAD) is a leading cause of death. Non-invasive techniques for screening patients for coronary artery disease are highly desirable.

At present the most widely used technique for assessing the existence of coronary artery disease is the "stress test" electrocardiogram (ECG). The ECG machine measures electrical signals generated by the heart, at the surface of the patient's body. These ECG signals are displayed to an attending physician for diagnostic use. The ECG waveform displays a characteristic shape, and each cardiac cycle includes P, Q, R, S and T inflection points which correlate to underlying cardiac events. In practice the patient's ECG is taken before, during and after vigorous exercise.

Strenuous physical exercise results in an increase in the patient's heart rate. An elevated heart rate can cause a transient ischemia in the myocardium if a major vessel of the heart is occluded by CAD. The reduction of oxygenated blood to the heart muscle itself affects both the mechanical and electrical properties of the heart muscle. In theory and practice the transient ischemia alters the conduction path of the depolarization wavefront over the myocardium. This abnormal conduction is usually reflected by abnormalities in the displayed ECG waveform. The most typical ECG abnormalities involve the "depression" of the S-T segment of the waveform, and the occurrence of low amplitude, high frequency electrical signals associated with the depolarization of the myocardium. The variability of these signals makes the analysis of the stress ECG highly subjective. Therefore the success of the screening procedure is highly dependant on the physician's skill. Although monitoring the electrical characteristics of the heart to ascertain the existence of coronary arteria disease is wide spread, the signals generated by the heart are ambiguous and difficult to interpret which is undesirable. For these reasons efforts have been directed toward other non invasive and non- electrographic methods of cardiac assessment.

For example, efforts have been directed at monitoring the actual motion of the ventricular wall of the heart to ascertain the existence of coronary artery disease. U.S. Pat. Re. 31,097 reissued Dec. 7, 1982, to Vas et al., shows apparatus capable of detecting the tissue movement of the heart by utilizing an electric field sensing apparatus adjacent to external areas of the body of the person being tested. This non-invasive technique results in a wall motion signal referred to as a "CKG".

In Vas this signal is displayed in real time in connection with a carotid phonocardiogram and a conventional ECG tracing.

The CKG apparatus of the prior art is very sensitive to the placement of the transducer which introduces additional variability in the measurement between pre-stress and post-stress measurements. Additionally, the real time display of the displacement signal does not exclude rate induced variations in the wave form nor are abnormally conducted beats excluded from the display data.

This prior art system exhibits many of the problems which must be addressed to produce a successful system for characterizing and displaying ventricular wall motion.

Like most signals of physiologic origin, there are beat to beat variations of the ventricular motion waveform which do not represent disease states. Other approaches to the direct measurement to ventricular wall motion for assessing myocardial ischemia are reviewed in *Ballistocardiography: Past, Present and Future* by Goedhard, published in Noninvasive Access to Cardiovascular Dynamics: Experimental and Applied Biblthca Cardiol., no. 37, pp. 27–45 (Karger, Basel 1979).

U.S. Pat. No. 3,695,253 to Vielhauer teaches the use of an accelerometer mounted at a patient's chest for measuring or indicating the blood pressure of a human subject or for detecting exact forces in the cardiovascular system of the patient. Like Vas, Vielhauer displays the output of the accelerometer sensor in real time in conjunction with a ECG waveform derived from the patient for diagnostic purposes.

U.S. Re. No. 27,042 issued Jan. 26, 1971 to Jorgensen, et al., discloses a method and apparatus for automatic screening of cardiac signals. The reference teaches time domain monitoring of low frequency compressional wave information. The preferred range is between 20 and 400 cps.

SUMMARY OF THE INVENTION

In contrast to these prior art references, the present invention detects cardiac induced compression waves, at the surface of the patient, through the use of a chest mounted inertial detector.

The compression wave information is collected along with an independent marker of underlying cardiac events. The preferred marker channel is a simultaneously recorded surface ECG.

Compression wave data and the ECG data are taken pre-exercise, post-exercise, and during recovery from exercise. The exercise protocol is designed to unmask CAD by inducing a transient ischemia which is reflected by changes in the electrical ECG data and in the mechanical cardiac compression wave data.

The ECG data is processed to identify cardiac cycles which result from normally conducted sinus depolarizations. The compression wave data, corresponding to these normally conducted sinus beats, are processed to extract and display the waveform features which are most strongly influenced by the exercise induced transient ischemia.

In use, pre-exercise, post-exercise, and exercise recovery compression waveforms are processed and displayed to the diagnostician for analysis along with a reference ECG.

BRIEF DESCRIPTION OF THE DRAWINGS

In the drawing, in which like reference numerals indicate corresponding structures throughout the views, in which.

DETAILED DESCRIPTION OF THE PREFERRED EMBODIMENT

The invention is described in connection with an illustrative embodiment which may be modified without departing from the scope and spirit of the invention.

Theory of Operation

The motion of body organs generates compression waves which are propagated throughout the body. Compressional waves are characterized by signal transmission in an elastic medium. The propagation of this type of signal is characterized by changes in volume and by particle motion parallel to the direction of wave movement. The human body may be considered very lossy transmission medium for such wave over a wide frequency range.

The principle generator for compressional waves in the human body in the very low frequency range appears to be the motion of the heart. It has been recognized that exercise induced transient ischemia can alter the pattern of mechanical motion of the heart. Experimental investigations suggest that the periodic compressional waves generated by the heart, are altered in a repetitive and reproducible way, by cardiac ischemia. Experimental data suggests that compressional wave data and ischemia induced variations in compressional wave data are best observed in the zero to thirty Hertz frequency range.

Even though the body is a very lossy transmission medium for the very low amplitude and very low frequency cardiac induced compressional waves, these compression waves may be reliably detected at the surface of the patient's body over the sternum with a suitable transducer. It appears that the sternum itself is a very well damped structure which collects and transmits the cardiac induced compressional waves with great fidelity. It also appears that other signal sources operating in this frequency range within the body are not readily detected from the sternum by the preferred transducer of the present invention.

DETAILED DESCRIPTION

U.S. patent application No. 07/234,031 filed Aug. 19, 1988, which is incorporated by reference, further describes the data collection and reduction system.

U.S. patent application Ser. No. 07/495,457, filed Mar. 16, 1990. Any alternative patch structure is taught by U.S. patent application ser. No. 07/611,932 filed Nov. 9, 1990, which is hereby incorporated by reference, which is incorporated by reference, further describes a transducer mounting plate which is useful for connecting the transducer to the chest.

Figure 1:
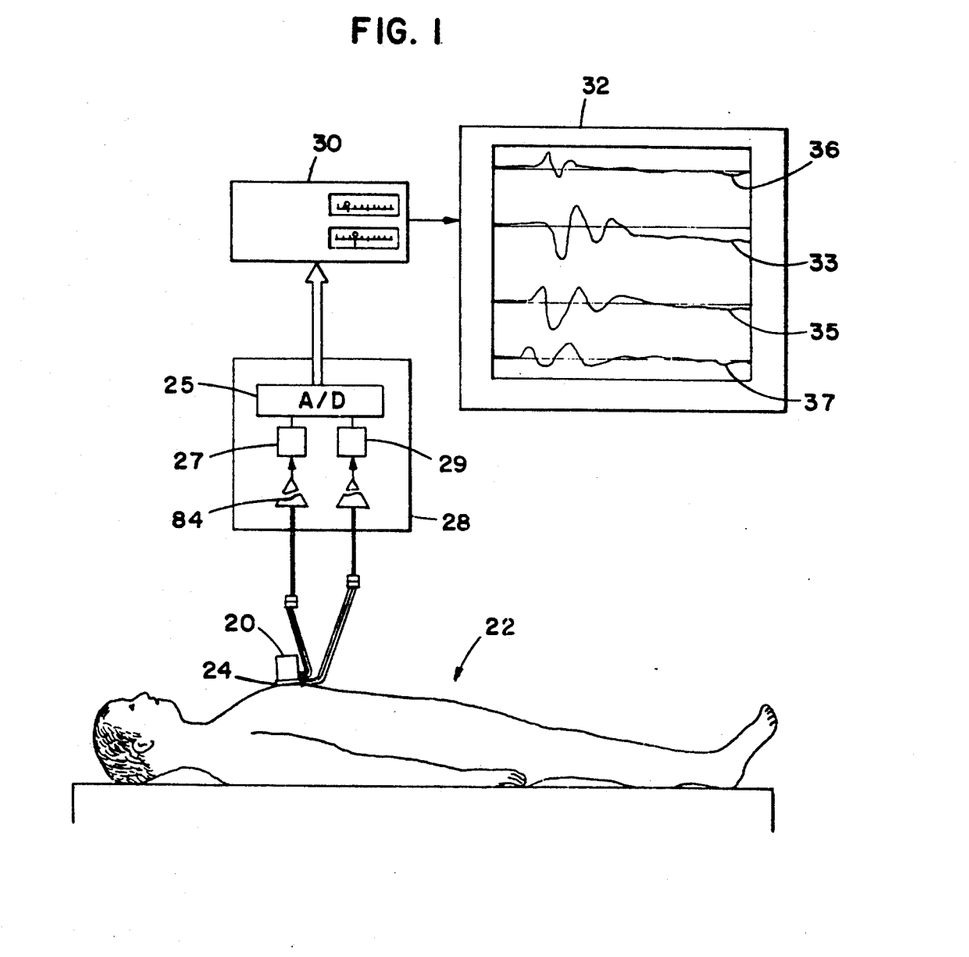
FIG. 1 is a block diagram depicting the major structure elements of the present invention.

FIG. 1 is a block diagram depicting the major structure elements of the present invention. The compression wave transducer 20 is mounted to a detachable mounting plate 24 which is adhesively fixed to the patient's 22 chest.

The mounting plate preferably incorporates an electrode array which is used to detect the surface ECG of the patient. However, the accelerometer may be used directly against the chest and a conventional electrode array may be used to collect the ECG signals.

In general, accelerometers are suitable for use as the compression wave transducer 20 in carrying out this invention. However, for the detection of ischemia induced variations in the compressional wave data, the accelerometer must have a wide bandwidth and should exhibit a flat frequency response from 0.025 hertz to 800 hertz. The accelerometer should also exhibit a high sensitivity of, for example, 1 microinch at 1 hertz. The mass of the transducer should be large enough to achieve these response characteristics when the transducer is placed on the chest of the subject. The mass of the transducer must be high enough to provide an inertial reference for the compressional wave data and, in effect, it must provide a good mechanical impedance match between the sensor and the patient's sternum It has been found that a mass between 1.0 lbs and 3.0 lbs is suitable for use with humans in a clinical setting. The mass appears to provide an inertial reference which causes the transducer to respond to a mathematical derivative of the motion of the heart, rather than the motion itself.

The purpose of the compression wave transducer is to translate with high accuracy the very low amplitude mechanical motion at the surface of the patient into an electrical signal for further processing. The extended, linear, high frequency response is required for high accuracy transcription of the subtle ischemia induced variations in the signal.

The preferred transducer for acquiring the cardiac motion signal from this location is an accelerometer such as the model 393C seismic accelerometer manufactured by PCB Piezotronics of Depew, N.Y.

The compression wave signals from the inertial transducer and the ECG signals from the electrode array are conducted to a signal conditioning module 28. After suitable amplification and buffering, the motion signal is digitized and processed under the control of a microprocessor.

It is preferred to use maximally flat bandpass filters on both the ECG channel and the compression wave channel. Preferred corner frequencies for the compression wave channel filter 27 are 0.3 and 50 hertz. Preferred corner frequencies for the ECG channel bandpass filter 27 are 0.05 and 160 hertz. The low frequency corner of the compression wave channel is the most critical of these parameters. The compression wave filter should be extended to as low a frequency as possible, consistent with transducer response and AC coupling requirements.

The compression wave information from the inertial transducer is digitized in a suitable A to D converter 25. In a similar fashion the corresponding marker channel data taken from the ECG channel is also digitized. This digitization process occurs at a fixed sampling rate and generates compression wave data and ECG data from the analog signals collected by the transducer and electrode array.

The digitized data is connected to a microprocessor system which may take the form of a computer 30 which is preferably an IBM AT or AT compatible Personal Computer. The computer operates on the data and generates processed data which is displayed on a suitable display 32. As shown in FIG. 1, it is preferred to display the composite ECG 36 along with pre-exercise 33, post-exercise 35 and recovery from exercise waveforms 37 for review and analysis.

In operation, the patient's underlying heart compression wave motion signal is monitored for approximately one minute. The corresponding marker channel data is analyzed to detect rhythm abnormalities. Segments of compression wave data are selected for averaging. These segments are selected to correspond to equivalent portions of the underlying cardiac cycle.

The averaging process uses a rate dependent measurement window. The R—R interval is measured and used to define a measurement window. Typically this window is approximately 13% of the measured R—R interval. In operation the R-wave inflection point for the normal sinus rhythm complex is then used as a fiducial point to direct data point selection in the compression wave data set. Typically 20% of the sampling points are devoted to the record prior to the R-wave inflection point, while 80% of the sampling points are devoted to the post R-wave record. This technique essentially removes rate based signal variations from the compression wave data. This technique also ensures that the data segments which are averaged arise from the same underlying cardiac events.

After a suitable number of measurements are made, the averaged compression wave form may be prepared for display, as shown at 36, 33, 35, and 37, to the physician for diagnostic purposes. It has been found to be useful to normalize the waveform amplitude so that the diagnostician is evaluating waveform morphology without regard to signal amplitude.

The use of a rate dependent measurement window also improves the signal-to-noise ratio of the displayed signal and, in particular, reduces rate induced signal variations in the displayed signal.

Figure 2A:
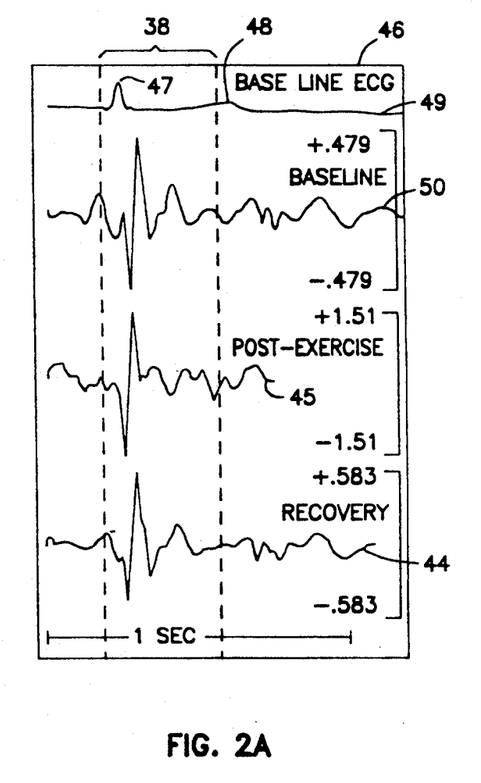
FIGS. 2A and 2B are a schematic representation of a diagnostic display from a normal patient exhibiting no coronary artery disease.
Figure 2B:
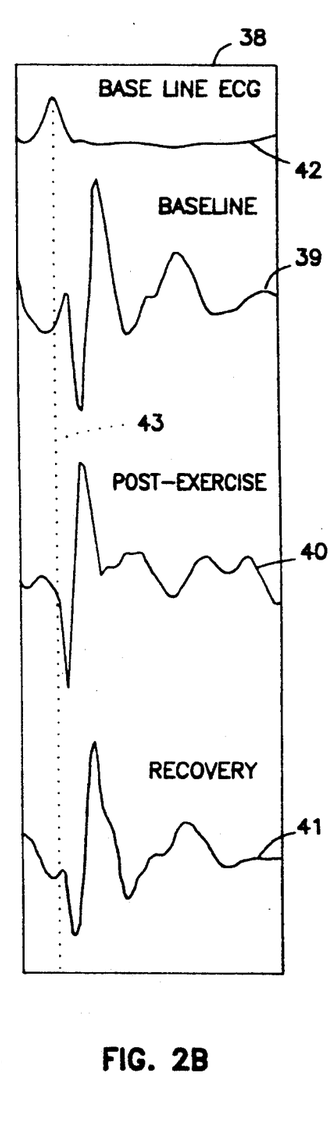

FIG. 2 is a schematic representation of a diagnostic display of a normal patient exhibiting no coronary artery disease. Panel A of the figure represents the diagnostic display presented to the physician, while an expanded version of the data analysis window 38, is shown separately as panel B of the figure. The data analysis window 38 displays the preexercise or baseline compression wave data 39; the postexercise compression wave data 40; and the recovery from exercise compression wave data 41. Also shown in the window is a composite ECG signal 42. The waveforms have been scaled to the same peak to peak values to more clearly reflect the compression wave morphology changes associated with ischemia. The window 38 reflects waveforms which indicate no underlying myocardial ischemia.

As previously described, the sampling process occurs at a fixed rate, while the patient's heart rate varies as a function of exercise. Consequently, the number of data points in a heart beat record may vary. This effect may be discerned from a comparison of the record length of recovery record 44 with the length of the post exercise record 45 shown in data reduction window 46.

It has been found that the greatest amount of information concerning myocardial ischemia is generated during the contraction of the ventricular muscles of the heart, during normally conducted heartbeats. Although the heart is in almost continual motion, the greatest ischemia induced variability in the compression wave signal occurs during the systolic time interval where the ventricles forcefully contract to pump blood throughout the body. The underlying electrographic waveforms which correspond to the systolic time interval extend from slightly before the electrographic R-wave 47 to the T-wave 48.

It is important to recognize that the compression wave data are taken at various times throughout the testing protocol and that the actual heart rate and systolic time interval corresponding to the selected beat can vary between records. Therefore pre-, post-, and recovery data sets will contain records of heartbeats which occurred at various rates and contain different numbers of sampling points, which need to be averaged.

To accommodate this variability in the records it is preferred to define a rate dependant window and to align heartbeat records within the window and to average selected portions of the candidate waveform data based upon a rate dependant timing window. In practice, the sample window is a function of the measured R—R time interval. The examples shown in the figures were generated with a window size equal to approximately 13% of the measured R to R interval for that heartbeat (window size in ms=(0.13(RR interval)+36.14 )). As the rate increases, the size of the window is reduced so that the sampling points are distributed over corresponding segments of the systolic time interval. The application of a rate dependant window for averaging data or for displaying data is illustrated in FIG. 7 and 8.

Figure 7:
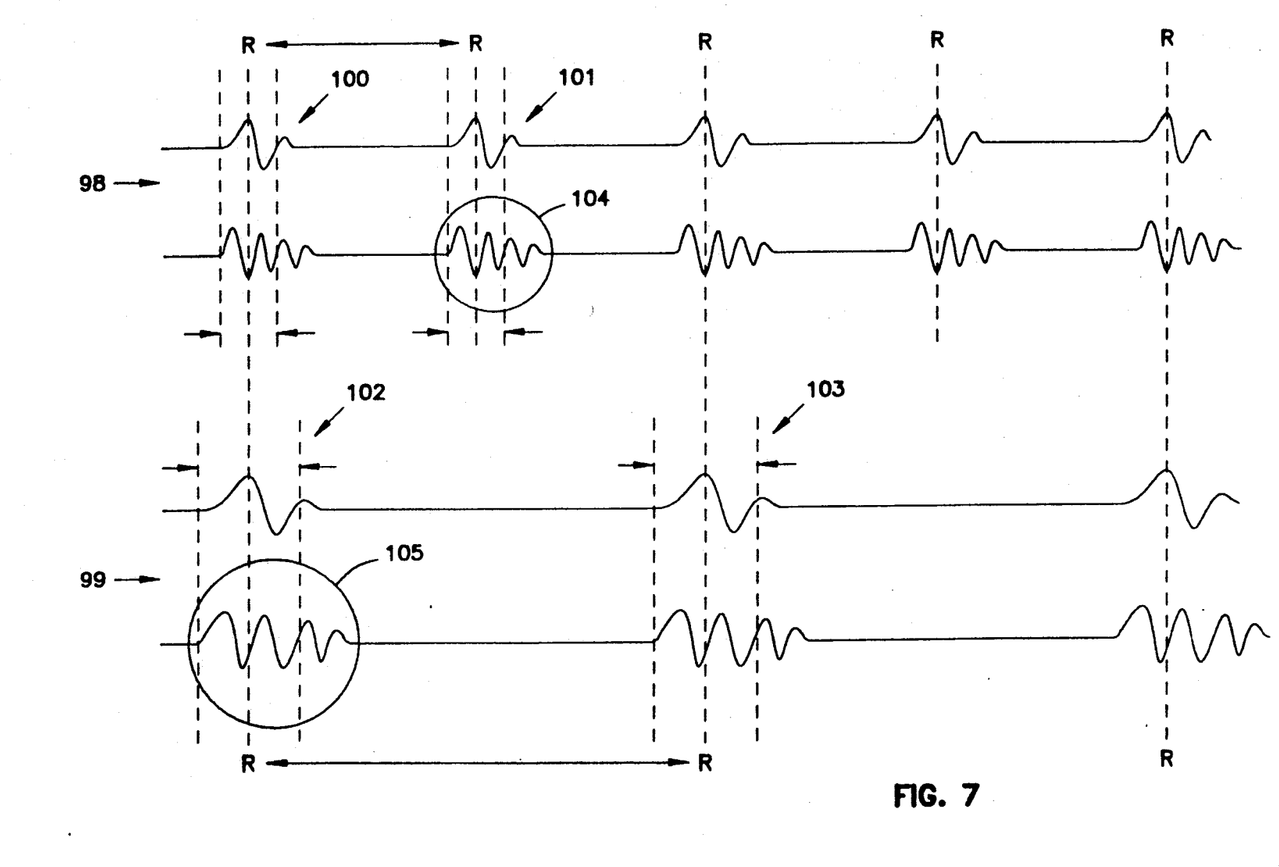
FIG. 7 is an idealized representation of the operation of the rate dependant averaging function, depicting simultaneously recorded cardiac event marker information and compression wave information.
Figure 8:
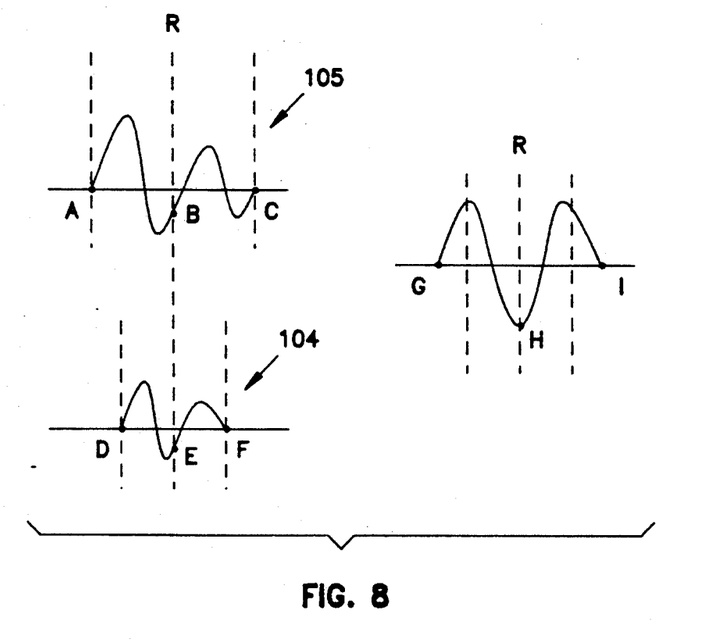
FIG. 8 is an illustration of the operation of the averaging process of compression wave data.

FIG. 7 shows two panels of simultaneously recorded ECG and compression wave data. The upper panel 98 shows the a heart rate which is twice the heart rate of panel 99. The complexes 100, and 101 occurring at the higher rate are narrower than the complexes 102, and 103 occurring at the lower rate of panel 99. However, if these records are taken during a single test session, for example post-exercise, then they must be averaged to generate a noise free composite record. Straightward averaging of complex 104 with 105 would obscure the subtle ischemia induced variations in the records. It is preferred to extract the electrographic R-wave as an index point or fiducial marker for the compression wave records, and then to align the records along the fiducial marker. A percentage of the waveform sampling points taken of the pre R-wave portion of the records are added together. In the figure point A would be added to point D and point B would be added to point E and point C would be added to point F. The arithmetic mean of these points is used to generate the composite waveform 106 containing points G, H, I. In practice, many waveform data points are extracted and averaged to generate the wave forms displayed on FIGS. 2 and 3.

Figure 3A:
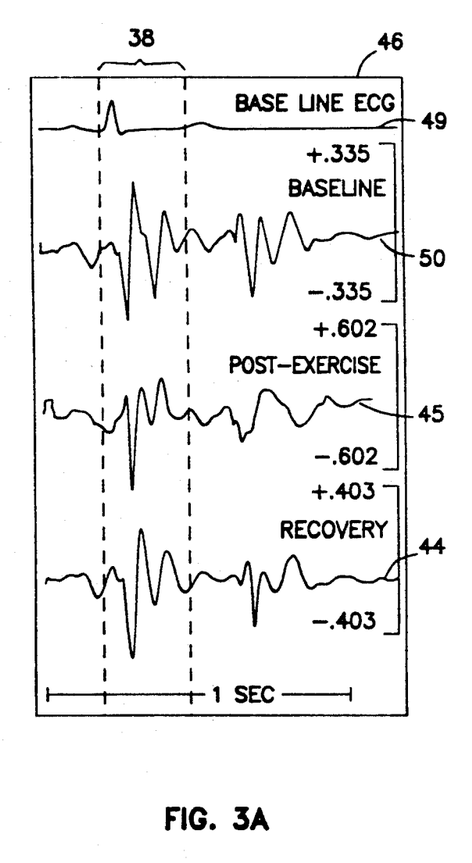
FIGS. 3A and 3B are a schematic representation of the diagnostic information from a patient exhibiting coronary artery disease.
Figure 3B:
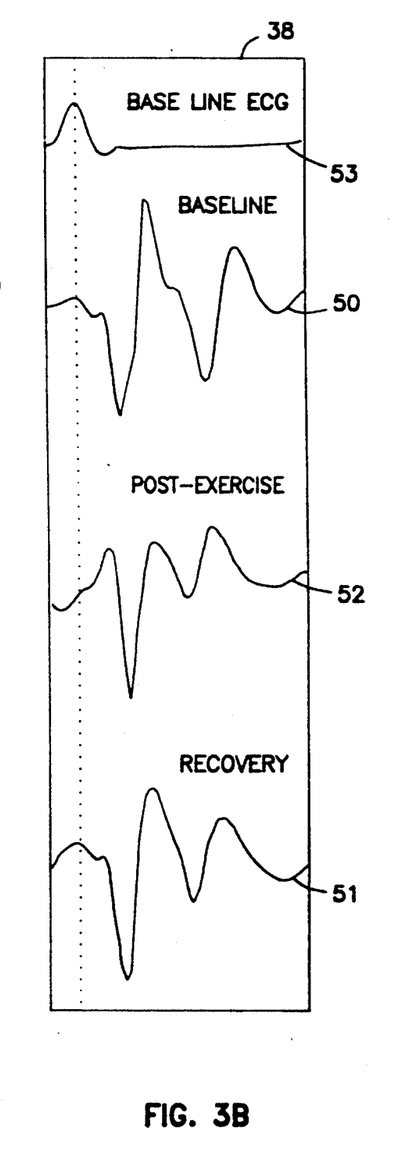

Panel A of FIG. 3 depicts the diagnostic display of a patient having coronary artery disease. Panel B is an expanded detail of the data analysis window 38 shown in FIG. 3A.

It is also useful to scale and normalize the displayed data to aid the diagnosticians review of the data. In the data reduction window 46 the records 50, 45, and 44 have been scaled or normalized for display within the data analysis window. In practice, the amplitude of the compression wave data varies as a function of heart rate. In the data reduction window, the displayed waveforms are normalized to the same magnitude, however the actual measured value of the peak to peak compression wave measurement is displayed in g units along the right hand edge of the display. For example, the averaged peak positive acceleration for the pre-exercise baseline waveform 50 is +0.479 g while the post-exercise waveform 45 displays an averaged peak positive acceleration of +1.51 g.

It is important to note that the scaled and normalized waveforms represent averaged wave data displayed in alignment with the electrocardiographic R-wave as shown by dotted fiducial line 43.

In practice the ECG records and compression wave records are linked or indexed so that the correspondence between the electrographic and compression wave data for each heartbeat are maintained.

The ECG channel data is used as an independent marker of cardiac events. In general, the marker channel is used to select segments of the compression wave data record for averaging.

The preferred and illustrative technique disclosed to achieve this result, uses waveform morphology and rhythm analysis of the ECG channel to select candidate cardiac cycles for further analysis.

The ECG channel data is processed to classify the cardiac beats as sinus rhythm or non-sinus rhythm and to extract the location of the electrographic R-wave in each heartbeat record. This R-wave is used as a fiducial point for processing the selected compressional wave data which occurs during the sinus beats.

FIG. 3 is a schematic representation of the diagnostic information for a patient exhibiting coronary artery disease.

In this example the baseline compression waveform 50 is very similar to recovery waveform 51. Both waveform 50 and 51 are markedly different from post-exercise waveform 52. Normalizing the compression waveform data to the same peak to peak values removes amplitude information from the display and reveals more clearly the waveform morphology changes which reflect the underlying disease. Inclusion of the ECG reference trace 53 orients the diagnostician and indicates the corresponding cardiac dynamics to the diagnostician.

It is known that ischemia and other disease conditions can cause abnormal beats such as Premature Ventricular Contractions (PVCs). Although PVC events may be used by a physician to assist in the evaluation of an ECG, these events are so mechanically dissimilar to normal rhythm and so dissimilar from each other that they contain no useful compressional wave ischemia information. For this reason PVCs and other non-sinus rhythms are excluded from the averaging process.

The principle requirement for a suitable cardiac marker channel for the present invention is the reliable exclusion of non-sinus beats. The low amplitude of the compression wave signal makes averaging very problematic if a PVC or other non-sinus beat is mistaken for a normal beat. Consequently the illustrative electrographic classifier strategy is biased toward exclusion of beats.

There are a variety of methods which may be used to exclude abnormally conducted beats, however it is preferred to exclude such beats based upon both rate and waveform morphology information.

Figure 4:
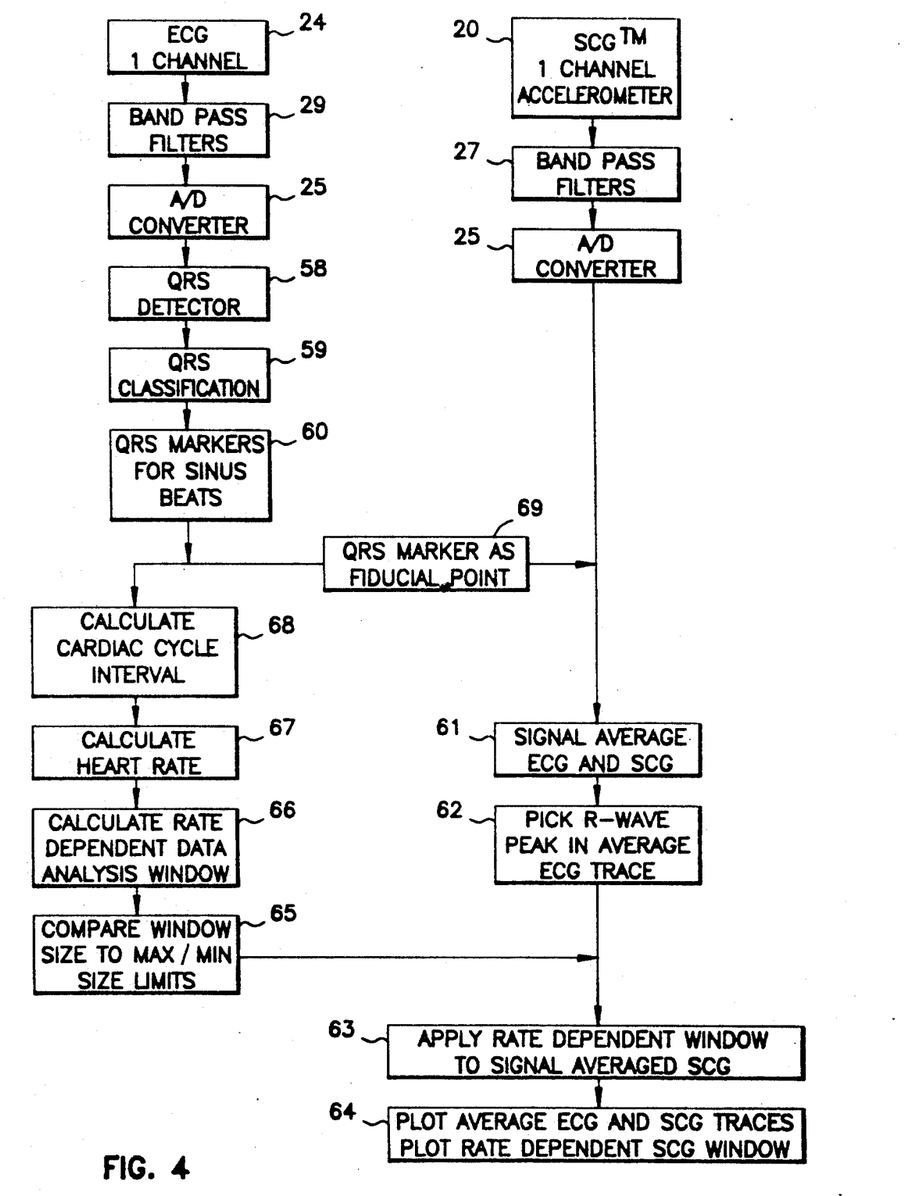
FIG. 4 is a system level flow chart depicting the operations, relationships and interaction between the structural elements of the invention.

FIG. 4 is a system level flow chart depicting the operations, relationships and interaction between the structural elements of the invention showing the relationship and partitioning between the hardware and software functions.

The surface electrodes of the mounting plate 24 collect the surface electrogram which is amplified filtered 29 and digitized 25 in hardware elements described in connection with FIG. 1.

QRS detection 58 may be performed in any of a variety of ways known to those skilled in the art. However, it is important to accurately ascertain the peak of the R-wave since this point is used as the fiducial point for averaging the compression wave data. In operation, the QRS detector 58 operates to ensure that the waveform sent to the classifier 59 reflects underlying physiological events. In this fashion it operates as gain control and filter for the digital waveform data taken from the surface of the patient.

QRS classification 59 is performed in software as set forth in connection with FIG. 5. Any of a variety of known electrographic techniques may be employed to recognize normally conducted beats. The principle requirement of this part of the system is, the inclusion of heartbeats which are initiated by a sinus node depolarization and, the exclusion of ectopic beats from the averaging process. The generation of QRS and PVC markers is used as an index to point to those compression wave records which correspond to the non ectopic sinus beats. Signal averaging at 61 may be performed in software. In general, the simultaneously recorded ECG and compression wave data are segmented into records corresponding to sinus rhythm. These records are aligned at the electrographic R-wave and are then averaged. It is preferred to use a large number of records (100) to compute an averaged ECG and an averaged compression wave waveform. The waveforms are averaged, with a rate dependant window which is applied to the averaged compression wave waveform at 63. The composite and averaged waveforms are also scaled by the application of the rate dependant window. Block 63 operates to select the ventricular contraction phase of the compression wave record for plotting. The plotting function 64 is invoked to scale and normalize the displayed waveforms. This process converts the waveforms so that the time base of the various records and the amplitudes of the various records are in essence removed from the records to accentuate the amplitude independent and time base independent changes in the compression waveforms.

Figure 5:
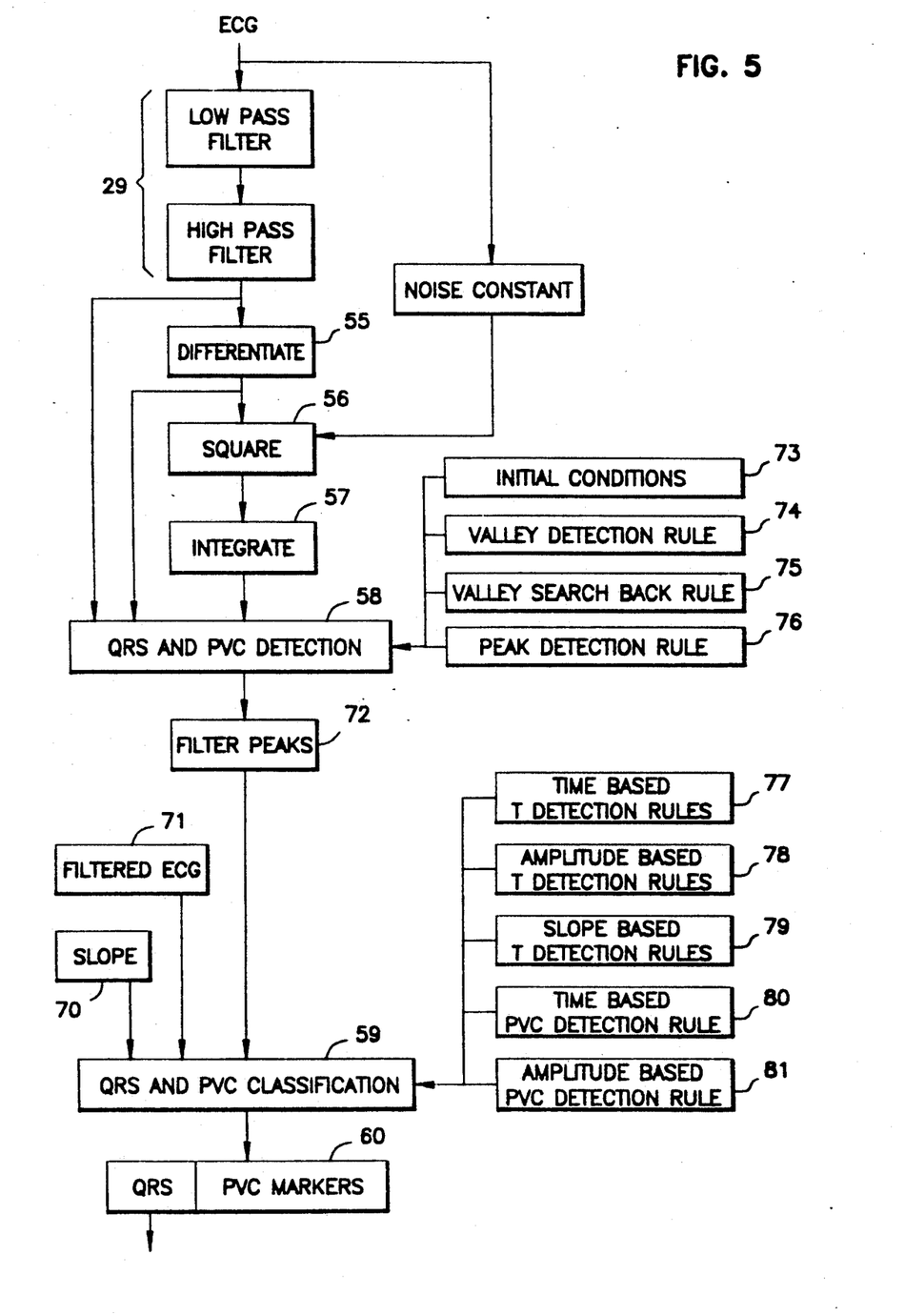
FIG. 5 is a flow chart showing the preferred QRS detection system used for excluding non-sinus beats from the diagnostic display.

FIG. 5 is a flowchart showing the preferred QRS detection system used for excluding non-sinus beats from the diagnostic display.

With respect to the ECG channel there are two requirements. It is desirable to transcribe the low level electrographic signal faithfully for waveform morphology analysis and for display to the diagnostician as shown by waveforms 42 and 53. Another requirement is the accurate determination of the position in time of the peak of the R-wave since this point is used as a fiducial marker for waveform averaging. The differentiation function 55 which may be performed in hardware or software, operates on the applied electrographic signals to accentuate the magnitude of the intrinsic inflection of the natural R-wave. The squaring 56 and integrating functions 57 restore the shape of the R-wave.

Thus the QRS detector 58 has both R-wave position information from the differentiation function 55 and waveform morphology information for detection purposes. The general function of block 58 is to screen and process the raw signals to ensure that they reflect physiologic data such as P, Q, R, S, T, and PVC waveforms and not periodic or random noise.

It is preferred to achieve this result through the application of valley search rules which analyze the data for significant slope reversals. An initial data point from the integrator is taken as a peak and subsequent data is searched for a peak which represents at least 25% of the preceding peak. This process removes short term low amplitude excursions from the waveforms presented to the classifier 59. a peak value is declared only after the value of the data has dropped to 59% of the maximum value of the peak. This strategy smooths the data. It is possible to vary these percentage values as a function of the data ensure extraction of waveform peaks which correlate to the underlying physiological waveforms.

Figure 6:
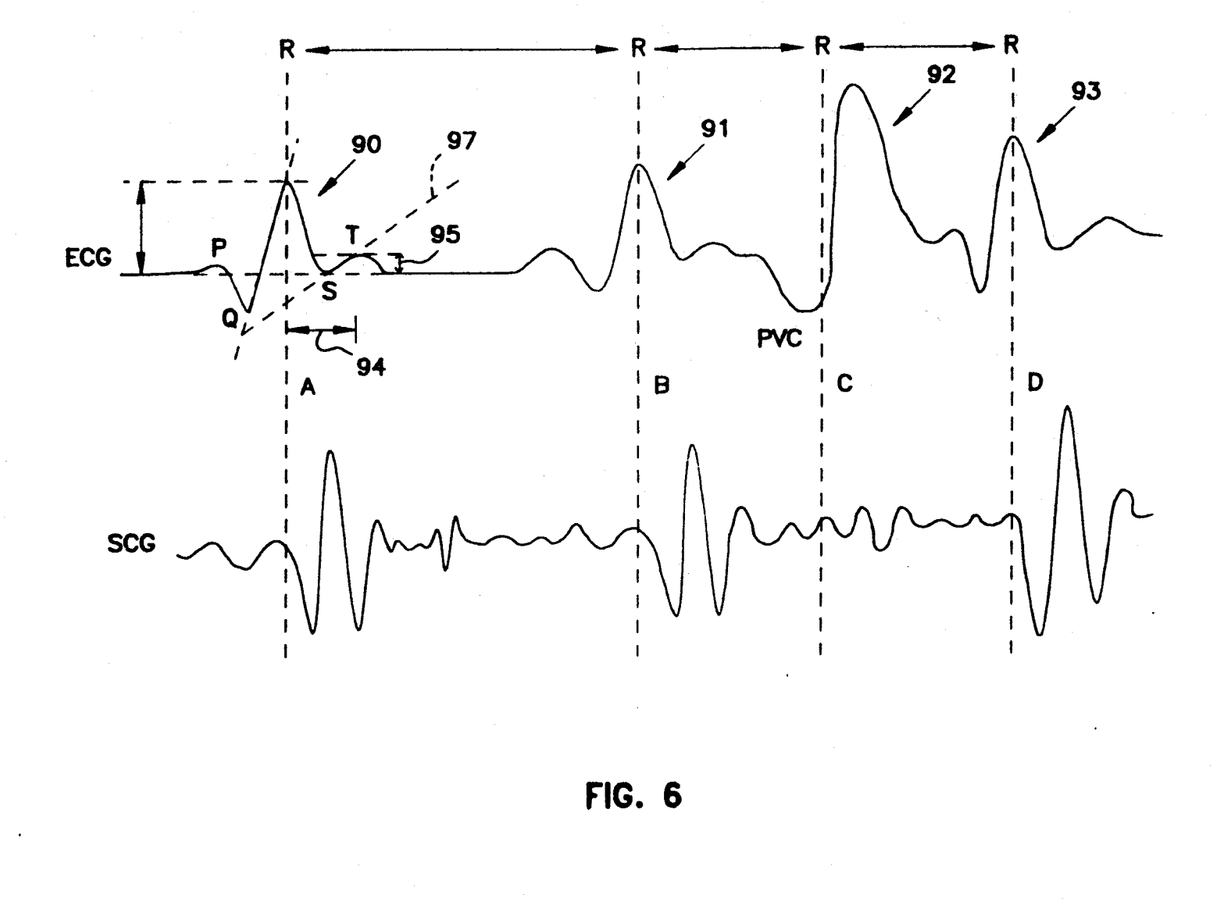
FIG. 6 is an idealized representation of the output of the detection system of the present invention.

FIG. 6 is an idealized representation of the output of the detection system of the present invention. Complex 90, 91, and 93 represent normal sinus beats. Complex 92 represents a PVC. In operation the ECG waveform of FIG. 6 is presented to the classifier 59, for the characterization of the waveform information contained in the ECG.

The classifier function 59 may employ a number of discrete detection criteria or rules. In general, all waveform peaks are partitioned into one of three classes. The waveforms are sorted into these classes based primarily on amplitude, time and shape information.

A "QRS" is classified as a peak which is not a PVC peak and which is not a T-wave peak. The preferred classification hierarchy proceeds as follows; a particular candidate peak is first tested for T-wave-ness based upon time, slope and amplitude information. If the candidate is not recognized as a T-wave, it is next tested for PVC-ness based upon time and amplitude criteria. A candidate waveform which is not a T-wave or a PVC is then classified as a QRS waveform. This process is skewed, to prevent misclassification of non QRS beats as QRS beats. This bias prevents corruption of the averaged waveform by ectopic beat compression wave data.

Although the preferred detection rules are further described, it should be apparent that a number of alternate techniques can be used to exclude non-sinus beats or to include only sinus beats.

More specifically, T-wave classification based upon time requires that a candidate T-wave peak occurs within 200 ms of the previous QRS or PVC peak as shown in FIG. 6 at 94. The amplitude based T-wave detection rule requires that the candidate T-wave maximum value 95 not exceed approximately 0.1825 of the averaged mean value of the preceding 7 QRS peaks 96. The slope based detection rule 97 requires that the peak T-wave occurs less than 300 ms from the previous QRS or PVC and that the maximum slope of the bandpassed signal 16 ms before the peak value is less than 75% of the maximum slope during the 16 ms preceding the previous valid QRS peak.

This is a particularly useful criteria since the T-wave repolarization pattern is not present in a premature ventricular beat complex. Therefore the existence and location of a T-wave segment is a particularly good indicator of a sinus beat.

It is also known that PVCs may occur prematurely in the rhythm. For this reason time based, rate and rate acceleration rules 77, 80 may distinguish PVCs and other tachyarrythmias from normal sinus rhythm. In general, all of these rules may be applied to insure the exclusion of non sinus beats or several of these rules may be added together to generate the QRS and PVC markers. It should also be apparent that numerous other rules may be invoked to discriminate the sinus from the non-sinus beats.

Biasing the classification system to exclude non sinus beats results in slightly extended data acquisition times. At present the system digitizes and stores approximately one minute of cardiac event marker data, and compression wave data. Data analysis takes place for approximately 7 seconds. During this interval, the historical records for compression wave information and cardiac event marker information are processed to select segments of the compression wave records which reflect compression wave data taken during the ventricular contraction phase of the cardiac cycle occurring in normally conducted beats.

What is claimed is:

1. Apparatus for the diagnostic display of a motion signal; characterizing ventricular wall motion of a patient's heart; from cardiac induced compression waves detected at the surface of said patient's body; to a diagnostician comprising:

compression wave monitoring means, responsive to compression waves at the surface of said patient's body, for generating a plurality of compression wave signals corresponding to said ventricular wall motion;

selecting means for detecting the systolic time interval of normal sinus beats of said patient's heart, and for generating a data collection window interval during such systolic time interval;

means for averaging said compression wave signals collected during said data collection window intervals; and for generating a composite wave form from said collected compression wave signals.

display means for presenting a representation of said composite waveform to said diagnostician.

2. Apparatus for the diagnostic display of a motion signal, characterizing the ventricular wall motion, of a patient's heart, derived from heartbeat induced compression waves detected at the surface of said patient's body, each heartbeat corresponding to the motion of the heart during one complete cardiac cycle, to a diagnostician comprising:

means for collecting compression wave information during cardiac heartbeats creating compression wave data;

means for selecting the cardiac contraction portion of said compression wave data for each heartbeat, creating a cardiac contraction compression wave record for each heartbeat;

means for averaging said cardiac contraction compression wave records, creating a composite compression wave record reflecting the ventricular wall motion of several heartbeats;

means for displaying said composite compression wave record to said diagnostician.

3. The apparatus of claim 2 wherein said means for collecting compression wave information comprises an inertial transducer responsive to motion at the surface of said patient.

4. The apparatus of claim 2 wherein said means for selecting the cardiac contraction portion of said compression wave data comprises:
   independent cardiac event marker means for indexing said compression wave data to underlying cardiac events;
   ventricular contraction detection means coupled to said independent event marker means for identifying said ventricular contraction portions of said compression wave data generating a cardiac compression wave record substantially corresponding to the ventricular contraction portion of said heartbeats.

5. The apparatus 2 wherein said means for averaging said ventricular contraction compression wave records, creating a composite compression wave record comprises:
   fiducial marking means for designating segments of said ventricular contraction compression wave records;
   arithmetic means for adding a series of said compression wave records indexed by said fiducial marking means, whereby said arithmetic means generates a composite compression wave record.

6 The apparatus of claim 2 wherein said means for generating a diagnostic display from said composite for display to said diagnostician, comprises:
   scaling means for plotting selected compression wave records on an arbitrarily selected time scale;
   normalizing means for plotting selected compression wave records on a arbitrarily selected amplitude scale.

7. Apparatus for the diagnostic display of a motion signal characterizing the ventricular wall motion, of a patient's heart, derived from cardiac heartbeat induced compression waves detected at the surface of a patient's body, each heartbeat corresponding to the motion of the heart during one complete cardiac cycle, to a diagnostician comprising:
   inertial transducer means responsive to motion at the surface of said patient, for collecting compression wave information during selected cardiac heartbeats creating compression wave data;
   means for selecting the cardiac contraction portion of each of said heartbeats, creating a cardiac contraction compression wave record for each of said selected heartbeats;
   means for averaging said cardiac contraction compression wave records, creating a composite compression wave record reflecting the ventricular wall motion of several heartbeats;
   means for displaying said composite compression wave record to said diagnostician.

8. Apparatus for acquiring cardiovascular diagnostic data from a patient's heart, and for displaying said diagnostic data to a diagnostician comprising:
   inertial transducer means, adapted to be coupled to the surface of said patient, for collecting compression wave data, arising from the motion of said patient's heart during a cardiac cycle of said patient's heart;
   cardiac event marker means for generating index data corresponding to selected portions of cardiac cycles of said patient's heart;
   processing means coupled to said inertial transducer means and coupled to said cardiac event marker means; for averaging a plurality of said selected portions of compression wave data generating display data;
   display means coupled to said processing means for presenting said display data to said diagnostician.

9. The apparatus of claim 8 wherein said processing means for averaging comprises:
   identifying means for identifying heartbeats arising from normal sinus depolarization of said cardiac tissue and for generating a set of candidate records, corresponding to compression wave data collected during said heartbeats arising from normal sinus depolarizations of said cardiac tissue;
   window means for selecting portions of said candidate records which include the ventricular contraction portion of heartbeats, arising from normal sinus depolarizations of said cardiac tissue, and for generating a set of windowed data records corresponding to compression wave data collected during the ventricular contraction portion of said heartbeats arising from normal sinus depolarizations of said cardiac tissue;
   computing means for generating display data corresponding to averaged data derived from said set of windowed data records.

10. Apparatus for detecting and characterizing the cardiac wall motion of a patient's heart comprising:
    independent marker means for generating a representation f said patient's cardic rhythm;
    seismocardiographic means for detecting compression waves resulting from cardiac wall motion;
    detector means, coupled to said independent marker means, for detecting individual beats of said patient's heart, and for defining a plurality of measurement windows, each window corresponding to one of said individual beats of said patient's heart;
    selector means for collecting seismocardiographic data during each of said measurement windows, generating collected seismocardiographic data;
    averaging means, coupled to said selector means for generating a composite representation of cardiac wall motion from said collected seismocardiographic data;
    diagnostic display means coupled to said averaging means for presenting said composite representation to said diagnostician.

11. The apparatus of claim 10 wherein said independent marker means comprises:
    electrocardiographic means for detecting the surface electrogram resulting from electrical activity of said patient's heart.

12. The apparatus of claim 10 further comprising:
    rejection means coupled to said independent marker means for excluding abnormal beats of said patient's heart;
    whereby said composite representation of cardiac wall motion excludes compression wave data generated by said abnormal beats.

13. The apparatus of claim 12 wherein said diagnostic display means displays said composite representation and displays said representation of said patient's cardiac rhythm.

14. The apparatus of claim 12 wherein said rejection means excludes non sinus heartbeats.

15. The apparatus of claim 12 wherein said rejection means excludes premature ventricular contract heartbeats.

16. Apparatus for the collection and display of data characterizing the motion of as patient's heart during heartbeat cycles, each heartbeat cycle corresponding to the motion of the heart during one complete cardiac cycle comprising:
   compression wave monitoring means proximate said patient's heart, for generating compression waveform data corresponding to the motion of said patient's heart during said heartbeat cycles;
   segmenting means for generating compression wavedata sets, each data set corresponding to heart motion during a portion of a heartbeat cycle;
   indexing means for defining fiducial points in each of said compression wave data sets;
   averaging means for collecting compression wave data sets and for averaging said compression wave data about said fiducial points, generating representative compression wave data;
   display means for generating a diagnostic representation of said representative compression wave data.

17. The apparatus of claim 16 wherein said compression wave monitoring means further comprises:
   classifying means for excluding compression wave data arising from non-sinus heartbeat cycles, from said averaging means.

18. The apparatus of claim 16 wherein said indexing means further comprises:
   means for establishing one of said fiducial points in each one of said compression wave data sets corresponding to a selected heart motion during one heartbeat cycle.

19. The apparatus of claim 17 wherein said indexing means further comprises:
   means for establishing one of said fiducial points in each one of said compression wave data sets corresponding to a selected heart motion during one heartbeat cycle.

20. The apparatus claim 16 wherein said averaging means further comprises:
   heartbeat rate detecting means for reducing rate dependent averaging error by assigning the set of fiducial points applied to a compression wave form data record as a function of the measured repetition rate of said heartbeat cycles.

21. A method for the collection and display of data characterizing the motion of a patient's heart comprising the steps of:
   (a) collecting compression wave data from the surface of said patient at a location near said patient's heart;
   (b) defining a set of compression wave records, each of said records corresponding to the motion of said patient's heart during one heartbeat cycle;
   (c) collecting a set of said heartbeat records corresponding to natural sinus rhythm of said patient's heart;
   (d) averaging said records collected in step (c) to form a representative record;
   (e) displaying data corresponding to said representative record.

* * * * *

UNITED STATES PATENT AND TRADEMARK OFFICE
CERTIFICATE OF CORRECTION

PATENT NO. : 5,159,932

DATED : November 3, 1992

INVENTOR(S) : Zanetti, et. al.

It is certified that error appears in the above-indentified patent and that said Letters Patent is hereby corrected as shown below:

Column 1, lines 6 and 7, please delete "patent application" and substitute therefor --Patent Application--

Column 1, lines 8 and 9, please delete "patent application" and substitute therefor --Patent Application--

Column 1, line 52, please delete the word "dependant" and substitute therefor --dependent--

Column 1, line 58, please delete the space after "-" and before "electrographic"

Column 2, line 28, after the word "for", please insert the word --monitoring,--

Column 3, line 3, please delete the word "drawing" and insert therefor --drawings--

Column 3, line 5, after the word "which", please insert --:--

Column 3, line 43, after the word "such", please delete the word "wave" and insert therefor --waves--

UNITED STATES PATENT AND TRADEMARK OFFICE
CERTIFICATE OF CORRECTION

PATENT NO. : 5,159,932
DATED : November 3, 1992
INVENTOR(S) : Zanetti, et. al.

It is certified that error appears in the above-indentified patent and that said Letters Patent is hereby corrected as shown below:

Column 4, lines 3, 6 and 8, please delete "patent application" and substitute therefor --Patent Application--

Column 4, line 7, please delete the word "Any" and substitute therefor --An--

Column 4, line 9, after "1990", please insert --(Attorney's Docket No. M&G 8789.2-US-01),--

Column 4, line 10, after "which is hereby incorporated by reference,", please delete "which is incorporated by reference"

Column 5, line 61, please delete the word "preexercise" and substitute therefor --pre-exercise--

Column 5, line 62, please delete the word "postexercise" and substitute therefor --post-exercise--

Column 6, lines 31, 34 and 43, please delete the word "dependant" and substitute therefor --dependent--

UNITED STATES PATENT AND TRADEMARK OFFICE
CERTIFICATE OF CORRECTION

PATENT NO. : 5,159,932

DATED : November 3, 1992

INVENTOR(S) : Zanetti, et. al.

It is certified that error appears in the above-indentified patent and that said Letters Patent is hereby corrected as shown below:

Column 6, line 45, please delete "FIG." and substitute therefor --FIGS.--

Column 8, lines 46 and 49, please delete the word "dependant" and substitute therefor --dependent--

Column 9, line 21, after "59", please delete "." and substitute therefor --,--

Column 11, line 18, in claim 5, after the word "apparatus", please insert the words --of claim--

Column 12, line 17, in claim 9, please delete the word "window" and insert therefor --windowing--

Column 13, line 5, in claim 16, please delete the word "as" and substitute therefor --a--

Column 13, line 14, in claim 16, please delete the word "wavedate" and substitute therefor --wave data--

Signed and Sealed this

First Day of February, 1994

Attest:

BRUCE LEHMAN

Attesting Officer

Commissioner of Patents and Trademarks